US008904852B2

(12) United States Patent
Wollny

(10) Patent No.: US 8,904,852 B2
(45) Date of Patent: Dec. 9, 2014

(54) METHOD FOR ESTABLISHING RHEOMETRIC PARAMETERS OF SAMPLES AND ROTATIONAL RHEOMETER

(75) Inventor: Klaus Wollny, Kirchheim Unter Teck (DE)

(73) Assignee: Anton Paar GmbH, Graz-Strassgang (AT)

( * ) Notice: Subject to any disclaimer, the term of this patent is extended or adjusted under 35 U.S.C. 154(b) by 131 days.

(21) Appl. No.: 13/196,451

(22) Filed: Aug. 2, 2011

(65) Prior Publication Data
US 2012/0024047 A1 Feb. 2, 2012

(30) Foreign Application Priority Data
Aug. 2, 2010 (AT) .................. A 1293/2010

(51) Int. Cl.
G01N 11/14 (2006.01)
G01N 11/16 (2006.01)

(52) U.S. Cl.
CPC .................. G01N 11/142 (2013.01)
USPC ........ 73/54.27; 73/54.01; 73/54.28; 73/54.32

(58) Field of Classification Search
USPC ........... 73/53.01–54.01, 54.23, 54.32, 54.27, 73/54.28, 54.31
See application file for complete search history.

(56) References Cited

U.S. PATENT DOCUMENTS

| | | | | |
|---|---|---|---|---|
| 4,095,461 A * | 6/1978 | Starita | ............... | 73/815 |
| 6,167,752 B1 | 1/2001 | Raffer | | |
| 6,499,336 B1 * | 12/2002 | Raffer | ........... | 73/54.28 |
| 6,571,610 B1 * | 6/2003 | Raffer | ........... | 73/54.35 |
| 6,952,950 B2 * | 10/2005 | Doe et al. | ............... | 73/54.01 |
| 6,962,086 B2 * | 11/2005 | Prescott et al. | ............... | 73/846 |
| 6,978,662 B2 * | 12/2005 | Platzek et al. | ............... | 73/54.42 |
| 7,194,895 B2 * | 3/2007 | Grey et al. | ............... | 73/54.23 |
| 7,249,523 B2 * | 7/2007 | Nickerson | ............... | 73/846 |
| 7,275,419 B2 * | 10/2007 | Raffer | ........... | 73/54.28 |
| 7,353,694 B2 * | 4/2008 | Grey et al. | ............... | 73/54.23 |
| 7,444,855 B2 * | 11/2008 | Cottais et al. | ............... | 73/54.39 |
| 7,784,329 B2 * | 8/2010 | Martinoty et al. | ........... | 73/54.01 |
| 7,992,427 B2 * | 8/2011 | Tonmukayakul et al. | ... | 73/54.28 |
| 2002/0178795 A1 * | 12/2002 | Isogai et al. | ............... | 73/54.23 |
| 2008/0022758 A1 * | 1/2008 | Cottais et al. | ............... | 73/54.32 |
| 2008/0078238 A1 * | 4/2008 | Stockhammer et al. | ..... | 73/53.05 |
| 2009/0320567 A1 * | 12/2009 | Takahashi et al. | ........... | 73/53.07 |
| 2010/0269571 A1 * | 10/2010 | Raffer | ........... | 73/54.28 |

FOREIGN PATENT DOCUMENTS

AT 404192 B 9/1998

* cited by examiner

*Primary Examiner* — David A Rogers
(74) *Attorney, Agent, or Firm* — Laurence A. Greenberg; Werner H. Stemer; Ralph E. Locher

(57) ABSTRACT

A method establishes rheometric parameters of samples using a rotational rheometer. A thickness of a measurement gap delimited by measurement parts is measured by a measuring unit and a predetermined thickness value is adjusted, readjusted or kept constant when the measurement temperature is changed or set to a predetermined measurement temperature setpoint value. Accordingly, starting at a time at which at least one region of a measurement part has reached the predetermined measurement temperature, measurement values to be established, more particularly continuously, at predetermined measurement times and/or for predetermined time intervals delimited by predetermined measurement times, for the changing thickness of the measurement gap and/or for the rate of change in thickness or readjustment of thickness, and for the measurement of the rheological parameters only to be commenced once these measurement values have dropped below a specific predetermined threshold.

15 Claims, 5 Drawing Sheets

METHOD FOR ESTABLISHING RHEOMETRIC PARAMETERS OF SAMPLES AND ROTATIONAL RHEOMETER

BACKGROUND OF THE INVENTION

Field of the Invention

The invention relates to a method for establishing rheometric parameters of samples and to a rotational rheometer for performing the method.

In order to determine the flow properties of complex liquids, solutions, molten materials, dispersions or gels up to solid bodies, all of which may more particularly not have ideal-viscous properties, rotational tests are often carried out using rotational rheometers. By way of example, such an instrument is described in AT 404 192 B.

The liquid and/or solid samples to be determined are introduced into the measurement gap, which is formed between two measurement parts with a defined geometry, in both conventional rotational rheometers and the rotational rheometers according to the invention. In order to carry out the test, differently shaped measurement parts may be attached at the provided actuating parts of the rheometer. The actuating parts are used to position the measurement parts relative to one another in the axial direction by means of mechanical elevating apparatuses, optionally by means of control electronics, and these parts thus form a measurement gap S with a defined height d. To this end, both positioning units with a precisely known linear advance and systems with an additional length-measuring system are known. The thickness of the measurement gap is determined using position sensors or distance sensors.

A shear stress is applied to the sample as a result of at least one of the measurement parts rotating and/or oscillating. Depending on the type of instrument, it is either the upper measurement part, e.g. as per Searle's method, or the lower measurement part, e.g. a measurement beaker, e.g. as per Couette's method, that rotates. The resistance exerted by the sample medium against this rotation and/or shear is expressed by torque acting on the measurement parts and is a measure for the rheological properties of the examined substance.

The resultant torque and/or the phase of the current recorded by the drive motor is determined and fed to an evaluation unit. Different embodiments of rotational rheometers with a combined drive and measurement motor are known, as are separate arrangements of drive and torque measurement by means of a separate measurement motor at the respective other measurement part.

The functional relationship between current recorded by the measurement motor and torque is known; the evaluation is then performed using a connected evaluation unit.

In the process, the measured rotational angle and the rotational speed of the drive motor, together with the acting torque, are translated into the rheological characteristics shear rate and shear stress, and these are used to calculate the viscosity of the examined sample. To this end, the remaining parameters of the system in addition to the gap width d must also be known, e.g. the aperture angle of the cone in the case of a conical measurement part and the radius thereof, or the radii of the measurement cylinders in a cylinder measuring system.

Tests may be performed with a prescribed shear rate, as can tests where a defined shear stress is prescribed; the test is carried out accordingly.

The values for the thickness d of the measurement gap S, measured using the position sensors, are linked in the evaluation unit to the measurement values relating to the torque of the substance to be examined and, if need be, are linked to the measurement values from a normal-force measurement apparatus that is used to establish the forces exerted on the measurement parts by the sample, and are used to calculate the viscosity.

In general, the following holds true for the shear viscosity η of ideal fluids:

η=shear stress τ/shear rate(γ)

In the case of a rotational viscometer, in which the height h of a sample or substance, which height results from the thickness of the measurement gap S and is found between a stationary measurement part (plate) and a measurement part (plate) with the radius R rotating relative thereto, is measured, the following relationships hold true for the shear velocity D and the viscosity η:

$$D_{(R)} = \frac{\omega * R}{h}$$

$$\eta = \frac{\tau}{D_{(R)}} = \frac{2*M}{\pi*R^3} * \frac{1}{D_{(R)}} = \frac{2*M*h}{\pi*R^4*\omega}$$

If e.g. a constant torque M is predetermined, a change in the height h results in the same proportional change in angular speed ω, as a result of which the calculated viscosity remains constant. However, if a change in height is not taken into account in the calculation, the following error emerges for the viscosity η:

If h'=k*h is used for the height (error factor k), the following emerges for the actual angular speed:

$$\omega = \frac{D_{(R)} * h}{R}$$

and the following emerges for the established viscosity:

$$\eta = \frac{2*M*h}{\pi*R^3*D_{(R)}*h} = C*\frac{h}{h} = C*\frac{1}{k}$$

H . . . calculated sample height [m]
h' . . . actual sample height [m]
$D_{(R)}$ . . . shear velocity at the radius "R" [1/s]
ω . . . calculated angular speed [1/s]
ω' . . . actual angular speed [1/s]
τ . . . shear stress [Pa]
M . . . torque [Nm]
η . . . viscosity [Pa·s]

The derivation above makes it clear that if there is a measurement error in the sample height, the viscosity changes inversely proportional to the height ratio, i.e. a measurement error in respect of the height of +1% results in a 1 percentage drop in the viscosity. The measurement gap generally has a thickness d of between 1 and 2 mm, as a result of which the gap thickness has to be determined with an accuracy that is better than 10 μm or 20 μm for keeping the error in the viscosity at <1%.

It is therefore important to keep the thickness d of the measurement gap S constant, and at least a readjustment is carried out.

In practice, there are also attempts to accommodate this fact by selecting a waiting period for a currently examined sample before the measurement starts, which waiting period is based on empirically established values or determined by preliminary tests on the material to be examined.

A proposed variant for checking the correct start time for a measurement uses two temperature sensors, respectively in the upper and lower measurement part of the rheometer, and determines when these both indicate the same temperature.

Moreover, it is proposed to control or regulate the sample heater using both elements. When the same temperature has been reached in the upper and the lower measurement part, the stable measurement time should have been reached. A problem with this procedure is that each thermo-element, e.g. a Pt 100, has its own characteristic, dependent on its properties, and must be adjusted by a comparison measurement, and thus adjustment and calibration between the two elements is always problematic; if the sample heater is regulated by these two elements, it is more likely that the temperature drift in the sample is increased.

BRIEF SUMMARY OF THE INVENTION

FIGS. 1 and 2 illustrate a rheometer that constitutes the starting point of the present invention and is based on the rheometer as per AT 409304 B1.

As mentioned previously, the invention is for example explained using a plate/plate measuring system, in which the sample 19 is situated between a lower measurement part 1b, embodied as a stationary plate, and an upper measurement part 1a, embodied as a rotating plate. Here, the rotating plate 1a may have smaller dimensions than the stationary plate 1b.

The measurement gap S can be set and determined indirectly using a length measuring system 12, 13, which has an accuracy of <1 μm. Detectors with a change in resistance (potentiometers), inductive position transducers (LVDT), or incremental position transducers or clock gauges can be used as length measuring systems. Instead of using a position measurement, a defined measurement gap S may also be set by driving a unit 50 in a height-adjusted fashion via the spindle 9 that has a known gradient by measuring the angular displacement of the spindle using an angular encoder 10. However, the disadvantage of this is that these systems determine the distance between the unit 50 and a stand 11 and not the thickness d of the measurement gap S directly. If the conditions of the surroundings are constant (constant room temperature, constant and equalized sample and measuring system temperatures), this can be used to actuate measuring system gaps with μm accuracy; however, practical experience shows that the change in the measurement gap can be a few 0.1 mm over the duration of the rheological measurement of a sample, which change is caused by the following influences:
thermal expansion and mechanical warping of the stand 11 and
thermal expansion of the measurement parts 1a, 1b and the shaft 3, with this having a very high influence when use is made of temperature chambers with a temperature range between −180° C. and 600° C.,
rigidity of the stand and rigidity of the shaft mount 5 because viscoelastic substances generate normal forces of up to a few 10 N when shearing.

Thus, high-end rheometers have a compensation apparatus that allows readjustment of the gap, for example by means of an empirically established temperature/position function, hence keeping the gap constant. In practice, this cannot realize sufficiently good compensation as a result of the generally unknown temperature equalization times, the multiplicity of measurement geometries and the different temperature chambers.

The thickness d of the measurement gap S is expediently established by a unit 22 formed by a position sensor, which directly measures the distance between the measurement parts 1a, 1b in a contactless fashion and, with the aid of the control unit 24, sets and/or readjusts said distance, and/or keeps it constant. A temperature measuring unit 21 is used to establish the temperature of the measurement part 1a.

An output signal X=f(S) is obtained from the measurement values; it specifies the distance between the measurement parts as a function of the thickness of the measurement gap S. Thus, the unit 22 provides an electrical signal that is related to the thickness of the measurement gap S by a known function. The output signals from the measuring unit 22 are fed to the control and evaluation unit 24 for further use, more particularly for adjusting or readjusting the measurement gap, or keeping it constant, or for evaluating measurement results and/or for calculating desired values, e.g. viscosity values.

Furthermore, the temperature-dependence of the output signals from the unit 22 should additionally be taken into account.

The temperature is measured using the temperature sensor 21, which can be placed into the unit 22 preferably formed by the position sensor, or as close to it as possible. The temperature measurement value is fed to a circuit 51 or the subsequent evaluation unit 24, as a result of which the influence of the temperature on the measurement value of the thickness d of the measurement gap S can largely be compensated for. The temperature dependence of the measuring unit 22 or the position sensor is established empirically during a reference run by passing over the temperatures within the application region at different constant gap dimensions.

By way of example, a reduction of temperature in the sample and/or in the surroundings thereof generally leads to a gap dilation; the samples contract and the dimensions of the measurement parts, the stand and the measurement shaft, which are predetermined by the thermal expansion, are reduced—seen overall the gap enlarges. The mechanical advance or the adjustment unit of the unit 50 thus must reduce the thickness d of the measurement gap S and acts in a direction of reduction of the thickness d in order to maintain a constant gap thickness.

Alternatively, heating the sample and/or the surroundings thereof leads to a narrowing of the gap, more particularly by a flow of the samples and expansions of the components of the rheometer, more particularly of the stand, the actuating parts and the measurement parts. In this case, the rheometer can react by mechanical readjustment with a view to gap dilation.

In both cases, the gap width is readjusted until a constant, set or predetermined measurement temperature is reached and thus the thickness d is readjusted counter to the change brought about by the temperature in order to keep the gap height constant.

A measurement now follows the following steps:
introducing the sample 19 between the two measurement parts 1a, 1b and setting the thickness d of the measurement gap S between the two measurement parts 1a, 1b to the desired gap thickness,
adjusting the temperature of the sample 19 by giving a temperature specification to a heating/cooling device (not illustrated) of the rheometer, wherein the
temperature is measured in the vicinity of the sample 19, or on the surface thereof, and/or on a measurement part 1a, 1b using the sensor 21 and, on the basis of this value, the
heating/cooling device with the control and evaluation unit 24 is regulated by means of the control and evaluation unit of the rheometer until the predetermined measurement temperature setpoint value is reached.

Here, the problem of when the measurement should be started is highlighted because setting or regulating the measurement temperature in the sample 19 is accompanied by changes in the thickness d of the measurement gap S. In order to determine the time for starting the measurement, a successful method of the type specified at the outset provides for, starting at the time at which at least one region of a measurement part has reached the predetermined measurement temperature or the temperature thereof has come within a predetermined temperature range of this measurement temperature, measurement values to be established, more particularly continuously, at predetermined measurement times and/or for predetermined time intervals delimited by predetermined measurement times, for the changing thickness of the measurement gap and/or for the rate of change in thickness or readjustment of thickness, and for the measurement of the rheological parameters only to be commenced once these measurement values have dropped below a specific predetermined threshold.

According to the invention, the temperature drift still present even after the sensor 21 has reached the measurement temperature setpoint value is monitored by observing the required thickness readjustment value of the measurement parts and/or the distance change or readjustment rate of the measurement parts and/or the changing distance per unit time between the measurement parts. The measurement values established for this allow a more precise prediction or determination whether the required temperature equalization, in the sample to be examined or for the measurement gap, has taken place and whether the entire system is stable. To this end, the thermal expansion rates $\Delta d/\Delta T$ of the entire system can be established because a temperature drift possibly present in the system causes a change in the sample geometry by the thermal change in the sample properties and in the rheometer geometry and thus there is also a change in the gap geometry. This change is compensated for by updating the mechanical elevating apparatus or the unit for setting the gap thickness. Within the scope of this check, reaching a desired accuracy class can be set and the achieved accuracy stage can be established using the greatest changes still remaining and can be displayed and evaluated. The measurement and the output of the rheological characteristics and/or the storage of the same in the evaluation unit are only commenced after this. Here, the entire procedure can be automated by the control and evaluation unit of the rheometer after an earlier selection of the accuracy class. Thus, provision is made for the difference value between the measurement values established at two measurement times to be respectively formed for two selected measurement times and/or a difference value of the measurement values established at the start and the end of a time interval to be formed for the selected time interval that is delimited by two selected measurement values, for the established difference value to be compared to a predetermined threshold, and for the adjustment or readjustment or constancy of the thickness of the measurement gap to be considered to have taken place and been sufficient depending on the comparison, and for the measurement of the rheometric parameters to be commenced, or for the method to be continued by establishing a further formed difference value and comparing the latter to the threshold and evaluating the comparison.

According to the invention, starting with a fixed time Z, the currently prevailing thickness d of the measurement gap S is established at predetermined time intervals, i.e. at specific measurement times, or the occurred changes in the thickness are measured at predetermined measurement times, or the respective rate of change in thickness are measured at specific measurement times or, for specific time intervals, the resulting change in thickness or the occurred rate of change in thickness is established for the respective time interval. These measurement values emerge from the adjustment movement, undertaken by the apparatus for keeping the measurement gap constant, for the two measurement parts 1a, 1b relative to one another, particularly if there is a readjustment of the measurement gap S to a constant value of the thickness d of the measurement gap S. The paths or rates at which the readjustment occurs, performed by the readjustment unit or the elevating apparatus which adjusts the unit 50, are established as measurement values at the respective measurement times or for the respective time intervals.

It is possible to form the difference values between measurement values established at respectively successive measurement times. It is preferable for the measurement values to be established at measurement times between which there is a number of further measurement times at which measurement values were also established, which, if need be, are also used for forming further difference values. The same applies for establishing the difference values for the measurement values established for the time intervals. Measurement values can, in principle, be established continuously. However, it is expedient to keep the clock times or time intervals between the individual measurement times relatively short and to select the measurement values for forming the difference values in such a way that there are longer time intervals between the times at which measurement values are selected to form the difference values than between the measurement times. It is expedient if the intervals between the measurement times themselves have the same duration and/or the time intervals for establishing the measurement values themselves respectively have the same duration and/or that the time intervals are delimited by the predetermined measurement times.

Provision is expediently made for the measurement values for the thickness and/or the readjustment values required for readjusting the thickness or keeping the latter constant and/or the required rate of change in thickness values established at the measurement times or for the time intervals to be used for forming difference values, optionally in such a way that these values were established at two selected measurement times, the time between which is calculated so that there is at least one further measurement time between these two selected measurement times, or these values were established for selected measurement times which lie at the start and at the end of a selected time interval formed by a plurality of successive time intervals. According to the invention, provision is made for the first measurement time and/or the start of the time interval for establishing the further difference value to be at a later time than the measurement time and/or the start of the time interval for which the previously compared difference value was established. As a result, the profile of the change in the measurement gap S is recorded until the undertaken readjustments drop below a predetermined threshold and are no longer considered relevant to the measurement.

It is expedient if the measurement values of the rate of change in thickness are established for selected time intervals that comprise at least two time intervals.

According to the invention, provision is made for a plurality of different-valued thresholds to be predetermined and for one of these thresholds to be used for the comparison depending on the desired measurement accuracy. By selecting the thresholds, the start of the first measurement is postponed until the measurement values or the difference values lie below a predetermined threshold, i.e. the change in thickness and/or the rate of change of the measurement gap lies below a predetermined value, as a result of which the accuracy class of the subsequently commenced measurement is set.

Furthermore, once the time Z is reached, provision can be made for the measurement parts and/or a sample chamber surrounding the sample to be thermostated and/or for the predetermined measurement temperature reached to be kept at a constant value. This largely minimizes a required readjustment of the measurement gap as a result of thermal influences.

According to the invention, a rotational rheometer according to the invention of the type specified at the outset is characterized
in that the control and recording unit comprises a measuring unit, by means of which, commencing at a specific time, measurement values are established, at predetermined measurement times, for the thickness and/or for the readjustment value that was required in a preceding time interval for compensating the change in thickness of the measurement gap and/or for the rate of change in thickness or readjustment of thickness of the measurement gap or for time intervals determined by the measurement times,
in that the measurement values are fed to a comparison unit, by means of which the respective values can be compared to a predetermined threshold,
and in that the output signal of the comparison unit is fed to the control and evaluation unit. It is advantageous for a difference former to be associated with the measuring unit, by means of which difference former difference values of measurement values, established at selected measurement times or for selected time intervals, are formed and these difference values are fed to the comparison unit.

In order to set the measurement times, provision is made for the measuring unit to comprise a clock generator for setting or determining the predetermined time intervals and the predetermined measurement times. This rheometer can further increase the measurement accuracy. Furthermore, the desired accuracy can be set or maintained in an improved fashion in this case. In order to set the accuracy classes for the measurement, provision is made for the comparison unit to have a threshold memory, in which a plurality of thresholds are stored.

The invention furthermore relates to a data carrier on which a program for carrying out the method according to the invention is stored, and/or a computer program with program code means designed for carrying out a method according to the invention if this program is executed on a computer, and/or a computer program, which is stored on a data carrier, and/or a data carrier with electronically readable control signals that can interact with a programmable computer system so that a method according to the invention is carried out. Finally, the invention relates to a computer program product with program code for carrying out the method according to the invention if the program is executed on a computer.

BRIEF DESCRIPTION OF THE SEVERAL VIEWS OF THE DRAWING

The invention is explained below in an exemplary fashion on the basis of the drawings.

DESCRIPTION OF THE INVENTION

Figure 1:
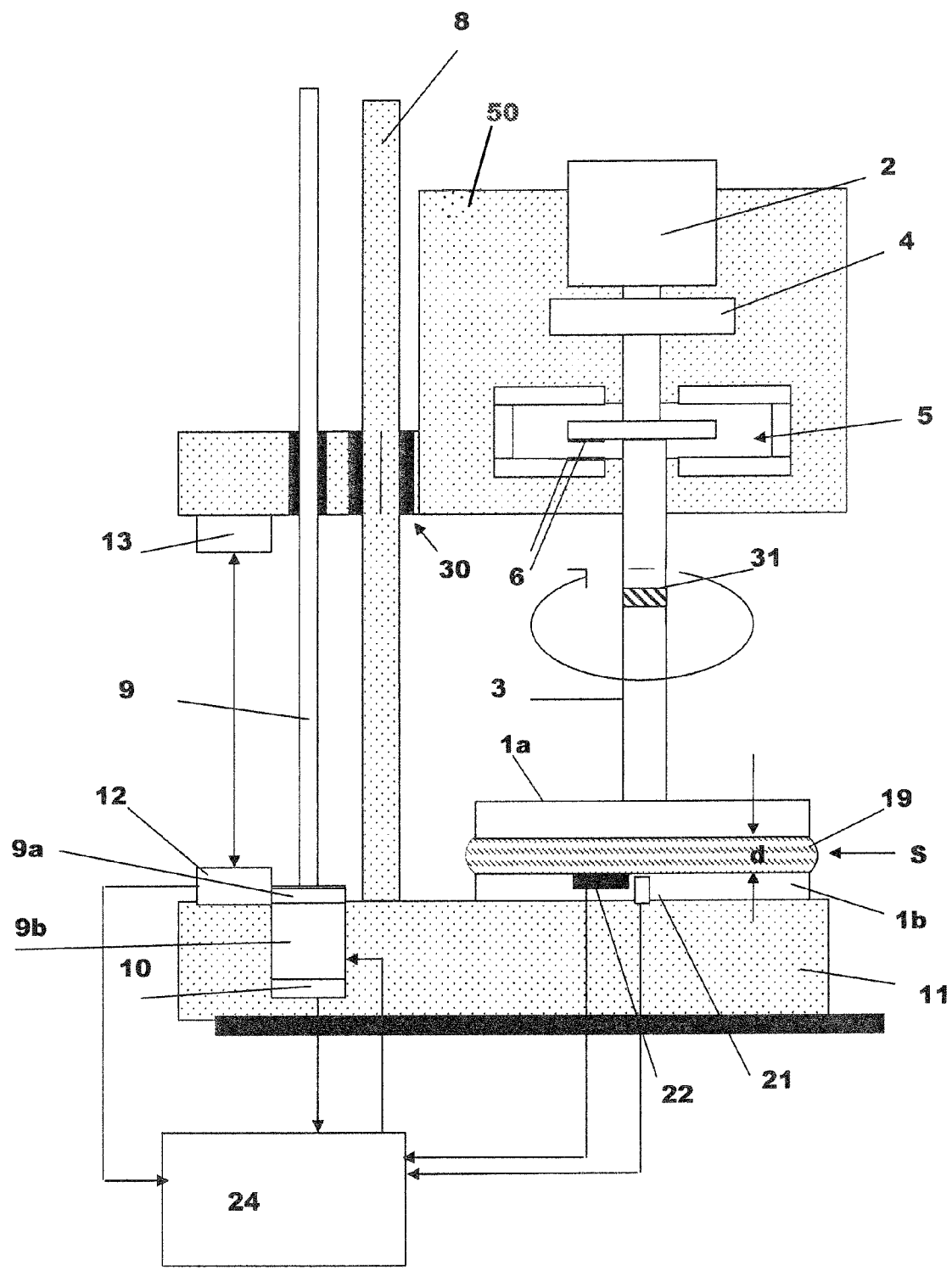
FIG. 1 shows a rheometer according to the invention.

As mentioned above, FIG. 1 schematically shows a rotational rheometer with a combined drive and measurement motor 2, a rotation and drive shaft 3, an angular encoder 4 and a frictionless bearing 5, which is illustrated here as an air bearing, schematically without supply lines. An apparatus 6 for measuring the normal force, which can be implemented with any type of measuring unit, is in this case embodied in the form of a position sensor or distance measurement instrument on the air bearing.

The measurement parts 1a and 1b, embodied as plates, can easily be replaced by way of a quick-release fastener 31 on the measurement and drive shaft 3 and an interchangeable mount for the lower measurement part 1b. The thickness of the measurement gap 5 is set by changing the height of an elevating platform 50, which is mounted so that it can be adjusted in terms of its height by being axially displaceable with respect to the stand 11. The sample 19 to be examined is situated in the measurement gap S between the two measurement parts 1a, 1b.

In general, the thickness d of the measurement gap S can be measured indirectly via the stand 11 and the column 8 and the unit or elevating platform 50 by using a length- or distance-measuring system 12, 13. Detectors with a change in resistance, inductive position transducers, incremental position transducers, clock gauges or the like can be used as length- or distance-measuring systems. Instead of using a position measurement, it is also possible to set a measurement gap S of a defined thickness d by adjusting the elevating apparatus 50 using a spindle 9 with a known gradient and a thrust bearing 9a and motor 9b and measuring the spindle angle using the angular encoder 10. However, other linear drives such as, for example, an Uhing linear-drive nut (rolling bearings), linear drives, pneumatically driven adjustment apparatuses, can also be used.

In alternative arrangements the lower measurement part may be embodied in a height-adjustable fashion and the upper measurement part and drive block are fixed on the stand.

Even a small change in the thickness d of the measurement gap S has an influence on the accuracy of the results from the rotational rheometer; according to the above equation, the gap width is included in the calculated result in respect of the viscosity and thermal effects play a large role.

In the case of a change in temperature, the change in the gap emerges as the sum of thermal expansion and mechanical warping of the stand 8, thermal expansion of the upper and lower measurement part 1a, 1b and the measurement shaft 3, and the rigidity of the stand and the stability of the mount.

High-end rheometers comprise a compensation apparatus, which readjusts the thickness d of the measurement gap S using an empirically established temperature/position function and thereby keeps it constant. It is also possible to determine the distance between the two measurement parts directly and to compensate for the changes in the gap thickness directly. Although the distance between the two measurement parts that form the measurement gap S is in this case still set by a mechanical elevating apparatus on the stand, the actual thickness d of the measurement gap S is no longer measured indirectly but rather directly and in a contactless fashion between the two measurement parts 1a and 1b. In the process, one of the two measurement parts carries the position sensor while the respective other measurement part carries the component influencing the position sensor or itself influences the component. The output signals from the position sensors are fed to the evaluation unit and thereby allow the distance between the measurement parts to be measured and/or set and/or kept constant. Advantageously, provision is made in this case for the output signals from the position sensors to be used to control an apparatus for modifying or setting or readjusting the measurement gap by adjusting the height of at least one of the two measurement parts. It is usually the height of the elevating platform that is adjusted.

Figure 2:
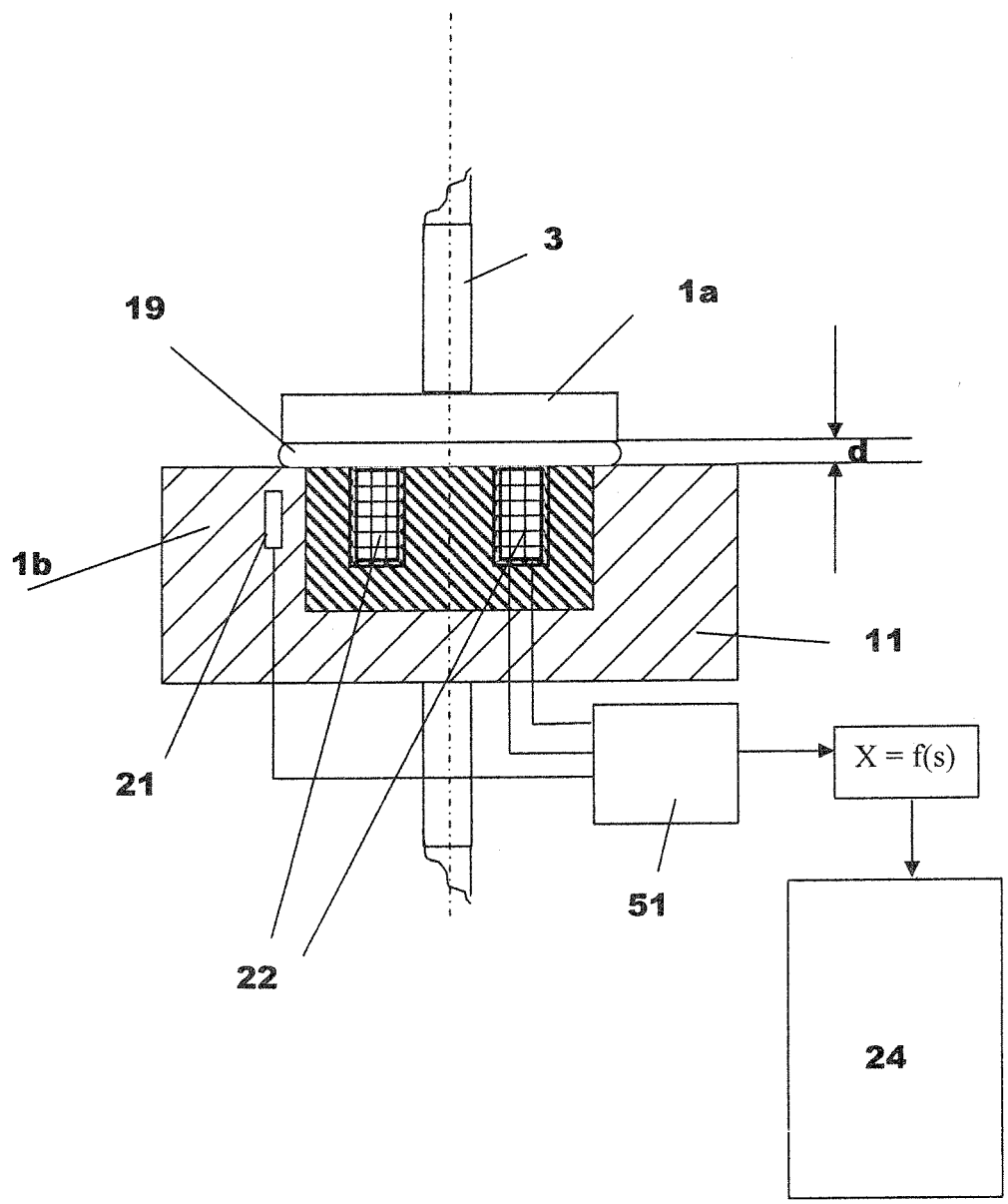
FIG. 2 shows a detail from FIG. 1.

FIG. 2 shows measurement sensors 22, operating on contactless principles, for the distance measurement that are integrated into the lower measurement part 1b, together with the temperature measurement element 21, which optionally corrects a temperature-dependent measurement value from the distance sensors operating on contactless principles as per the calibration and/or at the same time measures the sample and measurement-part temperature. The variable X established thus, which is a function of the distance s, is transmitted to the control and evaluation unit, optionally via the circuit 51 as linking unit, and is available there to correct the height or readjust the measurement instrument by means of the mechanical elevating system. By way of example, this variable can be the impedance value from an inductive sensor.

A temperature drift of the system, which has a negative influence on the measurement accuracy, can thereby be compensated for by adjusting or setting the measurement parts using the unit for mechanical gap adjustment.

The sample temperature is an important parameter in many test setups. The properties of substances are characterized as a function of their temperature; by way of example, temperature-dependent flow limits can be established by tests in temperature-controlled chambers and/or measurement parts. It is usual for use to made of temperature chambers with selectable test temperatures in the range between −180° C. and 600° C. or more; measurement parts and chambers with Peltier elements, electrical heaters and temperature-controlled gases streaming through them are part of the prior art.

In general, the sample temperature in one of the two measurement parts 1a, 1b or in the vicinity of the sample is measured by means of a thermo-element 21 (see FIGS. 1 and 2) and the temperature chamber and/or heating device of the measurement parts is controlled or regulated thereby.

A certain amount of time passes after a temperature change in the sample, set by means of a heating element in a measurement part and/or in a temperature chamber, until the sample reaches the setpoint temperature. In addition to the selected measurement body and the gap geometry, the thermal conductivity and/or heat capacity of the sample also play an important role in this case. Temperature chambers with a uniform heating of sample and/or measurement parts 1a, 1b and measurement shaft 3 in particular can take a relatively long time until thermal equilibrium is reached at the set temperature.

Structurally stable samples are measured a number of times and, in the process, the measurements take place or the viscosity values are evaluated in the evaluation unit until the established values of the viscosity no longer exhibit drift, as a result of which a number of tests are conducted.

Particularly in the case of materials whose structure changes during the measurement, such as e.g. polymers, pseudoplastic samples with long relaxation times such as e.g. yoghurt, the multiple-measurement path is unavailable because of course each individual measurement changes the sample and hence influences the result. In this case the invention provides a remedy.

Figure 3:
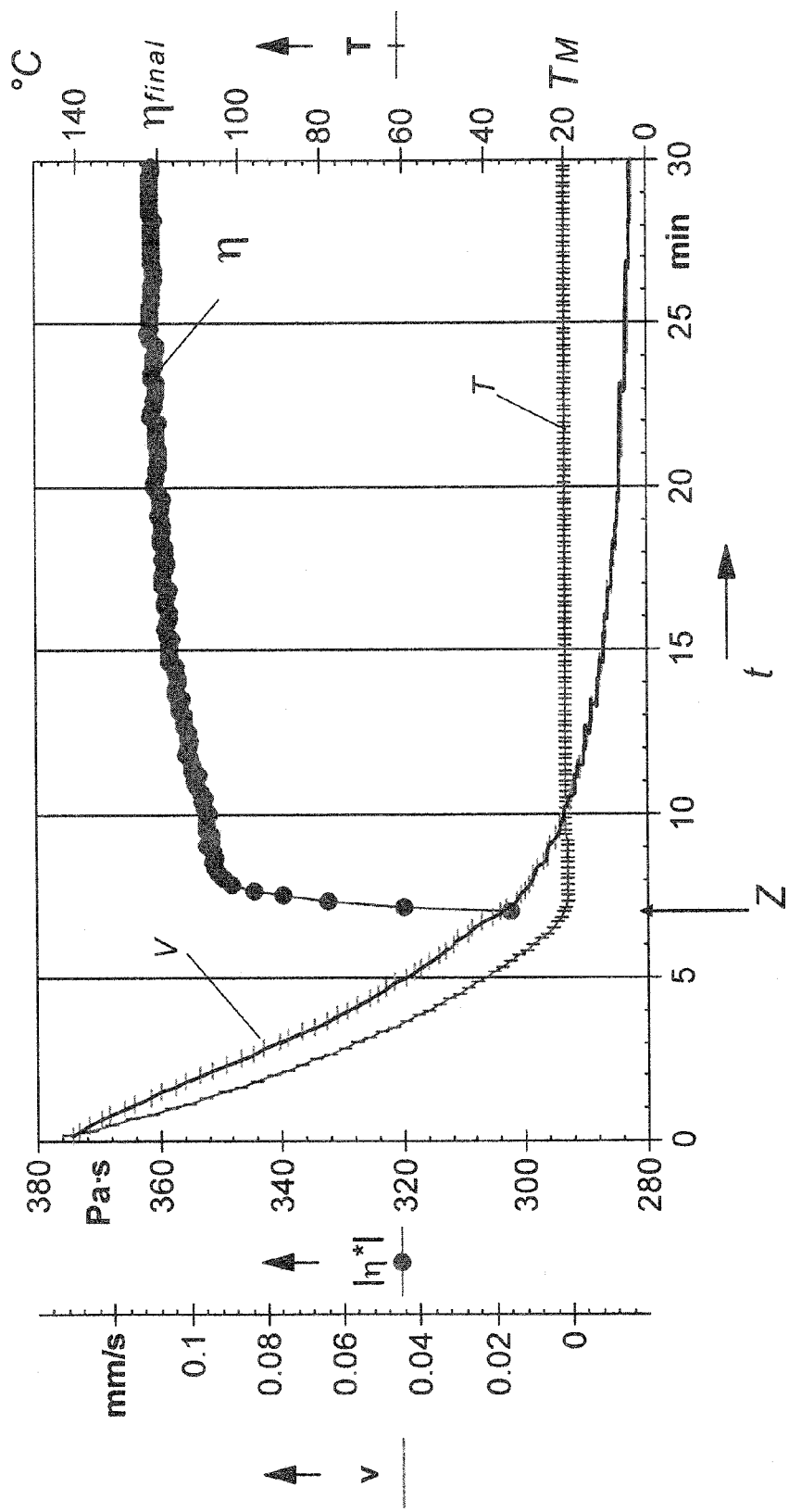
FIGS. 3, 4 and 5 show graphs relating to measurement value profiles.
Figure 4:
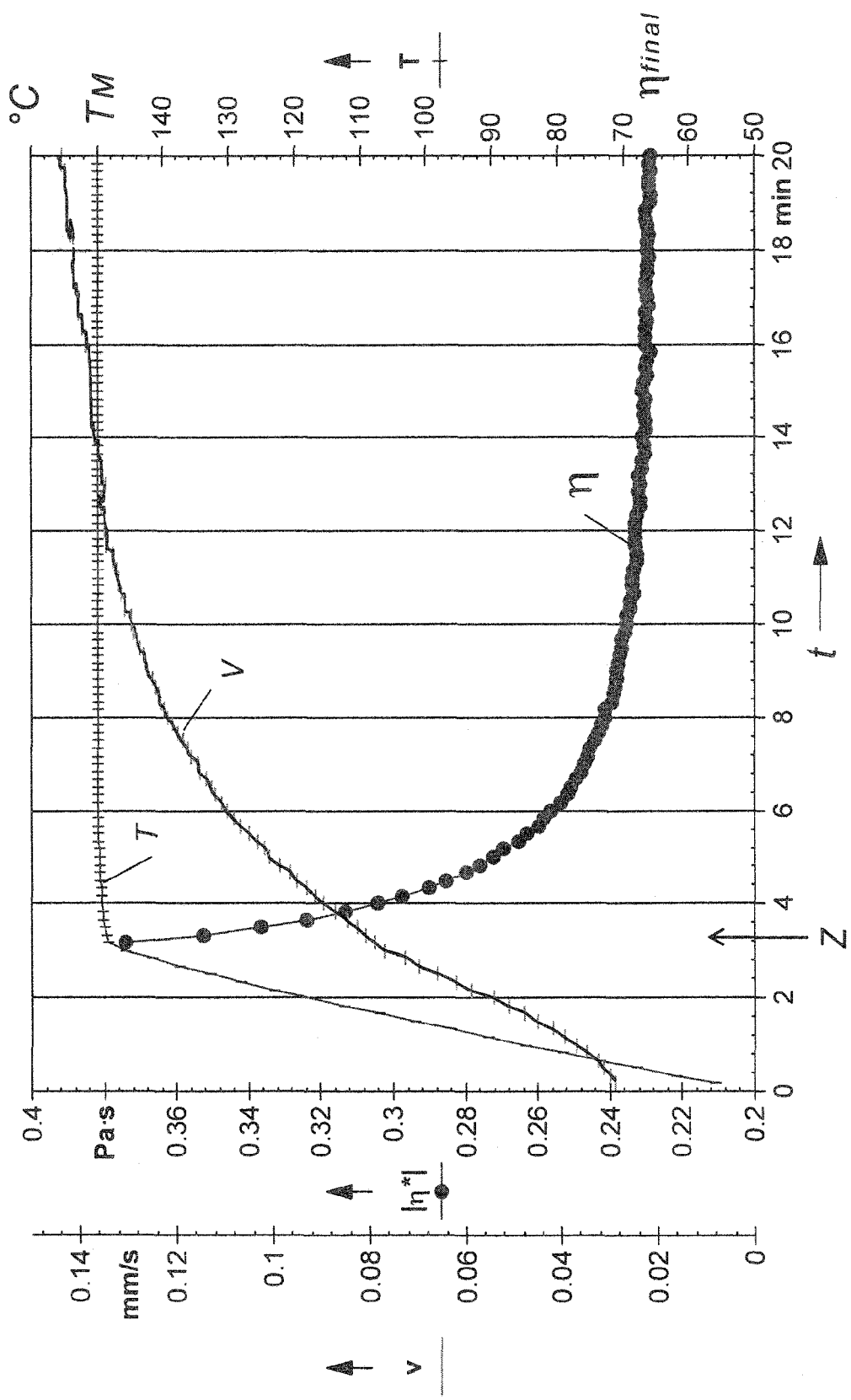

FIGS. 3 and 4 show, for two different gap widths and samples with poor thermal conductivity, the development of the viscosity $\eta$ measured using a rotational rheometer, for example as per AT 409304 A1, and the thermal expansion rates V of this system as speed of the gap readjustment ($V=\Delta d/\Delta t$) after a temperature jump, plotted against time t. The temperature measurement values T of the sensor 21 show the development of the temperature in the vicinity of the surface of a measurement part. While the gap thickness is kept constant by the control unit 24, the variable $V=\Delta d/\Delta t$, relating to the speed or the movement prescriptions of the mechanical elevating system 9, 9a, 9b, 10 that continuously readjusts the gap thickness, clearly shows the ever-slower setting or readjustment of the measurement gap S.

In FIG. 3 the sample 19 in a measurement gap S with a gap width or thickness of d=0.047 mm is cooled to 20° C., starting from a temperature of 150° C. Once this setpoint temperature $T_M$ has been reached at the temperature sensor 21, the viscosity measurement of a structurally stable sample 19 was initiated and the control variable of the elevating or gap-regulating system 50 was recorded in order to establish the rheological parameters. While the temperature T measured by the sensor element 21 from this time onward remained constant, the continuing change in the gap, or the profile of the required readjustment as a result of the slower setting-in of thermal equilibrium in the sample or in its surroundings, can clearly be identified. The readjustment rate v is specified as a measurement value for the readjustment.

The diagram clearly indicates the correlation between the measured viscosity $\eta$, which as expected approaches the base or final value $\eta$. Final after reaching thermal equilibrium in the sample 19, and the measured change or expansion rate of the gap system. This means that a measurement of the parameters at the time Z was started prematurely.

In the case of FIG. 4, a sample 19 was heated to 150° C. in a gap with a 1 mm gap height, starting from 50° C.; the correlations can also be clearly identified in this case. The gap thickness has not yet reached the predetermined end value at the time Z. As a result of the thermal changes in thickness in the sample, and changes in lengths of the individual components in the system, the readjustment rate still changes over a significant amount of time. The measurement temperature was reached after approximately 3 min; the readjustment of the measurement gap has not been fully completed after 20 min. The readjustment rate and the paths required for this decrease more and more, and so the ever decreasing readjustment values can be neglected after a certain selectable time when a desired accuracy for measuring the parameters has been reached. The still occurring readjustment rate could be neglected after approximately 20 min and the measurement of the parameters could be started.

Depending on the desired accuracy of the measurement, the measurement is started for the current change in the gap after reaching the required or desired temperature equalization, or after reaching and/or over or undershooting a predetermined threshold (depending on position and selection).

In an advantageous embodiment variant, checking or time intervals are to this end defined with a constant duration, e.g. of 200 seconds, and the gradient of the readjustment rate determined in this selected time interval and/or the associated change in thickness of the measurement gap is established and treated as a linear function. The gradient of the movement curve in this time interval may be used as a measurement value. To this end, the gradient of the equilibrating curve over the measurement values in the time interval is calculated or the difference-value-of-the-gradient measurement values are established at the start and end of the time interval, and a comparison is made as to whether these are already smaller than a predetermined threshold for a desired accuracy class.

By way of example, the threshold for gap movement can be set to be <2 µm/200 s for a standard measurement and less than 0.5 µm/200 s for the precision measurement.

In the process, a new selected measurement interval is started at a small time interval to predetermined measurement times, for example measurement values are established every 10 seconds, i.e. the measurement values of the gap movement are established e.g. every 10 seconds for a selected time interval, or for a selection of selected time intervals, of e.g. 200 seconds and the measurement value established for the entire selected interval is used for comparison purposes. This means that the measurement values are used for forming a plurality of selected intervals, which intervals are successively formed, offset in time.

Figure 5:
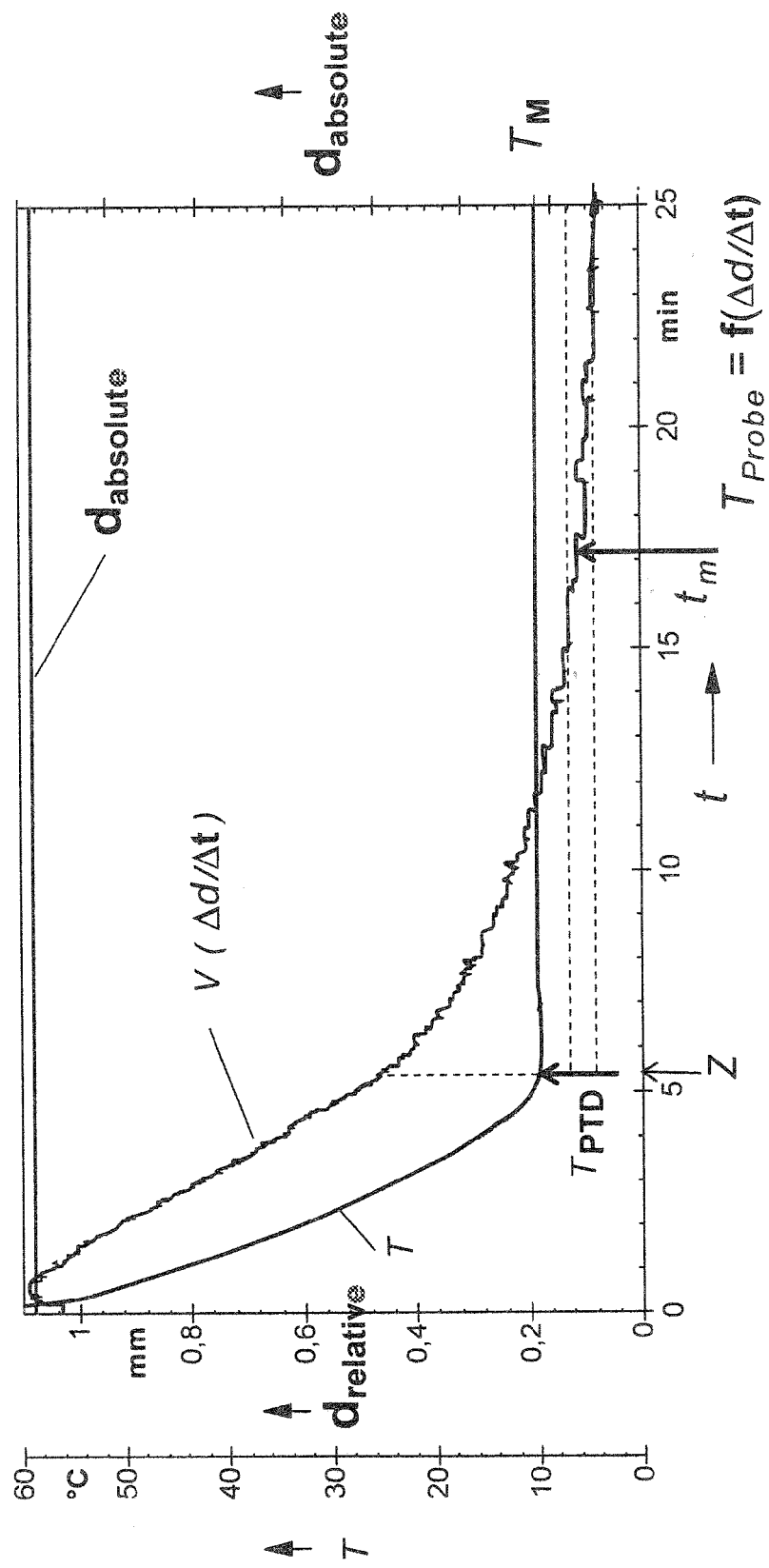

FIG. 5 shows a diagram in which the absolute thickness $d_{absolute}$ of the measurement gap S and the relative thickness $d_{relative}$ or the rate of change in thickness and the temperature T are plotted over time t. Once again, it can be seen that the gap thickness has not yet reached its final value at the time Z, and that the readjustment of the gap or the rate of change in thickness values approach a minimum after approximately 20 min. Hence, a measurement with a predetermined accuracy could be commenced at the time $t_M$.

By predetermining constant selected time intervals and establishing the changes in the gap thickness resulting for these time intervals, e.g. 200 seconds, the difference values $\Delta d/\Delta t$, established for the respective time intervals and formed using the measurement values at the start and at the end of the respectively selected time interval, and the threshold can be set side by side and the difference value is compared to the threshold value.

Provided that there are time intervals of equal length, the change rate for readjusting the measurement gap directly after the time Z is greater than for a time interval that is considerably later than the time Z; the same holds true for the distance of the gap thickness from the desired value of the gap thickness. In the latter time interval, the change of the measurement value for the readjustment rate is substantially lower than in the first time interval, which occurs directly after the time Z. Comparing the measurement or difference values obtained for the first and for the latter time interval with one and the same threshold may result in the threshold being considered overshot for the first measurement interval and undershot for the latter measurement interval. By way of example, the time $t_m$ in FIG. 5 could be a suitable time for measuring the parameters.

Provision can be made for a time interval to be formed with a predetermined number, which is kept constant, of measurement values, starting from the time Z. By way of example, such a time interval could contain 20 measurement values, for example the measurement values 1 to 20. A subsequently formed time interval could contain the measurement values 2 to 21, the next time interval could contain the measurement values 3 to 22, and so selected time intervals are always available, the measurement or difference values of which can be compared to a threshold selected for a desired accuracy class.

The specified difference values should be understood to mean the change values of the measurement values for specified time intervals. These difference values can be formed from the thicknesses d of the measurement gap S, measured at the start and the end of the selected time interval. This difference value may also be a change in the readjustment rate, established at the start and at the end of the interval for the rate of the readjustment or for the entire time interval. Such a difference value can be formed by the changes in the thickness values of the measurement gap, measured at the start and at the end of the time interval. Depending on the duration of the interval, or the time between the measurement times, there are difference values with greater or smaller gradients. More particularly, it is expedient to approximate the measurement curves emerging from the readjustment of the gap thickness by straight lines for specific time intervals so that the calculation of the difference values is simplified.

The invention claimed is:

1. A method for establishing rheometric parameters of samples using a rotational rheometer, wherein a thickness of a measurement gap delimited by measurement parts is measured by a measuring unit and a predetermined thickness value is adjusted or readjusted or kept constant when a measurement temperature is changed or set to a predetermined measurement temperature setpoint value, which comprises the steps of:

starting at a time at which at least one region of a measurement part has reached a predetermined measurement temperature or its temperature has come within a predetermined temperature range of the predetermined measurement temperature, measurement values are established, continuously, at predetermined measurement times and/or for predetermined time intervals delimited by predetermined measurement times, for a rate of change in thickness or readjustment of the thickness of the measurement gap, and a measurement of the rheological parameters is only commenced once the measurement values have dropped below a specific predetermined threshold.

2. The method according to claim 1, wherein:

a difference value between the measurement values established at two measurement times is respectively formed for two selected measurement times and/or a difference value of the measurement values established at a start and an end of a time interval is formed for a selected time interval that is delimited by two selected measurement values, an established difference value is compared to a predetermined threshold, and the adjustment or readjustment or constancy of the thickness of the measurement gap is considered to have taken place and been sufficient depending on a comparison, and the measurement of the rheometric parameters is commenced, or the method is continued by establishing a further formed difference value and comparing the latter to the threshold and evaluating the comparison.

3. The method according to claim 1, characterized in that the times between the predetermined measurement times and/or the predetermined time intervals amongst themselves are selected to have the same duration and/or in that the predetermined time intervals are delimited by the predetermined measurement times.

4. The method according to claim 1, characterized in that the measurement values for the thickness and/or the readjustment values required for readjusting the thickness or keeping the latter constant and/or the required rate of change in thickness values established at the measurement times or in the predetermined time intervals are used for forming difference values, wherein, optionally, these values were established at two selected measurement times, the time between which is calculated in such a way that there is at least one further measurement time between these two selected measurement times, or these values were established for selected measurement times, which lie at the start and at the end of a selected time interval formed by a plurality of successive time intervals.

5. The method according to claim 1, characterized in that the first measurement time and/or the start of the time interval for establishing the further difference value is at a later time than the measurement time and/or the start of the time interval for which the previously compared difference value was established.

6. The method according to claim 1, characterized in that the measurement values of the rate of change in thickness are established for selected time intervals that comprise at least two time intervals.

7. The method according to claim 1, characterized in that a plurality of different-valued thresholds are predetermined and one of these thresholds is used for the comparison depending on the desired measurement accuracy.

8. The method according to claim 1, characterized in that once the time is reached, the measurement parts and/or a sample chamber surrounding the sample are thermostated and/or the reached, predetermined measurement temperature is kept at a constant value.

9. The method according to claim 1, characterized in that the measurement signal from the measuring unit is temperature-compensated for establishing the thickness of the measurement gap.

10. The method according to claim 1, characterized in that, starting at the time, the temperature drift of the thickness of the measurement gap, i.e. the changes in thickness of the measurement gap caused during its adjustment to the measurement temperature as a result of the change in the temperature of the sample, and the change in the thickness of the measurement gap continue to be measured and the thickness is continuously updated or adjusted to the predetermined thickness value.

11. Rotational rheometer with a control and recording unit for the rheometric parameters of a sample derived by the measurement parts, with a measuring unit for establishing the thickness of the measurement gap delimited by the measurement parts, and with an actuation unit, controlled by the measuring unit, for setting or readjusting the thickness to, or keeping it constant at, a predetermined thickness value by modifying or adjusting the distance between the measurement parts, characterized in that the control and recording unit comprises a measuring unit, by means of which, commencing at a specific time at which at least one region of a measurement part has reached a predetermined measurement temperature or a temperature of the at least one region has come within a predetermined temperature range of the predetermined measurement temperature, measurement values are established, at predetermined measurement times or for time intervals determined by the measurement times, for the rate of change in thickness or readjustment of thickness of the measurement gap, the measurement values are fed to a comparison unit, by means of which the respective values can be compared to a predetermined threshold, and the output signal of the comparison unit is fed to the control and evaluation unit.

12. The rotational rheometer according to claim 11, characterized in that a difference former is associated with the measuring unit, by means of which difference former difference values of measurement values, established at selected measurement times or for selected time intervals, are formed and these difference values are fed to the comparison unit as measurement values.

13. The rotational rheometer according to claim 11, characterized in that the measuring unit comprises a clock generator for setting or determining the predetermined time intervals and the predetermined measurement times.

14. The rotational rheometer according to claim 11, characterized in that the comparison unit has a threshold memory, in which a plurality of thresholds are stored.

15. A non-transitory data carrier on which a program for carrying out a method as per claim 1 is stored.

* * * * *